(12) United States Patent
Wach et al.

(10) Patent No.: US 9,920,344 B2
(45) Date of Patent: Mar. 20, 2018

(54) OPTIMIZED METHOD FOR PRODUCING A COMPOSITION CONTAINING ISOMALTULOSE

(71) Applicant: Südzucker Aktiengesellschaft Mannheim/Ochsenfurt, Mannheim (DE)

(72) Inventors: Wolfgang Wach, Worms (DE); Thomas Rose, Worms (DE)

(73) Assignee: SÜDZUCKER AKTIENGESELLSCHAFT MANNHEIM/OCHSENFURT, Mannheim (DE)

( * ) Notice: Subject to any disclaimer, the term of this patent is extended or adjusted under 35 U.S.C. 154(b) by 0 days.

(21) Appl. No.: 14/905,325

(22) PCT Filed: Jul. 17, 2014

(86) PCT No.: PCT/EP2014/065358
§ 371 (c)(1),
(2) Date: Jan. 15, 2016

(87) PCT Pub. No.: WO2015/007833
PCT Pub. Date: Jan. 22, 2015

(65) Prior Publication Data
US 2016/0160251 A1    Jun. 9, 2016

(30) Foreign Application Priority Data

Jul. 18, 2013 (DE) .................. 10 2013 011 977

(51) Int. Cl.
| | | |
|---|---|---|
| *G01N 33/554* | (2006.01) | |
| *C12P 19/24* | (2006.01) | |
| *C12P 19/12* | (2006.01) | |
| *C12N 11/04* | (2006.01) | |
| *C12N 11/02* | (2006.01) | |

(52) U.S. Cl.
CPC .............. *C12P 19/12* (2013.01); *C12N 11/02* (2013.01); *C12N 11/04* (2013.01); *C12P 19/24* (2013.01); *C12Y 504/99011* (2013.01)

(58) Field of Classification Search
CPC .......... C12P 19/12; C12P 19/24; C12N 11/02; C12N 4/04; C12Y 504/9904; G01N 33/554
USPC .......................................... 435/7.32, 94, 100
See application file for complete search history.

(56) References Cited

U.S. PATENT DOCUMENTS 4,359,531 A * 11/1982 Bucke ...................... C12N 9/90
426/536
4,386,158 A *  5/1983 Shimizu .................. C12P 19/12
435/100

FOREIGN PATENT DOCUMENTS

| CA | 1179283 A | 12/1984 |
|---|---|---|
| CA | 2254956 A1 | 11/1997 |
| EP | 0 049 801 A2 | 4/1982 |
| EP | 0 091 063 A2 | 10/1983 |
| EP | 0 483 755 A2 | 5/1992 |
| EP | 0 625 578 A1 | 11/1994 |
| EP | 0625578 B2 | 11/1994 |
| EP | 1 424 074 A1 | 6/2004 |
| EP | 0 794 259 B1 | 10/2004 |
| JP | H4-169190 A | 6/1992 |
| WO | 97/44478 A1 | 11/1997 |

OTHER PUBLICATIONS

International Search Report from Corresponding Application No. PCT/EP2014/065358; dated Oct. 14, 2014.
De Oliva-Neto et al.; "Isomaltulose Production From Sucrose by Protaminobacter Rubrum Immobilized in Calcium Alginate"; Bioresource Technology; vol. 100 No. 18; Sep. 1, 2009; pp. 4252-4256.
Kawaguti et al.; "Production of Isomaltulose Using Erwinia Sp. D12 Cells: Culture Medium Optimization and Cell Immobilization in Alginate"; Biochemical Engineering Journal, vol. 29 No. 3; Apr. 15, 2006; pp. 270-277.
Krastanov et al.; "Conversion of Sucrose Into Palatinose in a Batch and Continuous Processes by Immobilized Serratia Plymuthica Cells"; Enzyme and Microbial Technology; vol. 39 No. 6; Oct. 3, 2006; pp. 1306-1312.
International Preliminary Report of Patentability from Corresponding Application No. PCT/EP2014/065358; dated Jan. 19, 2016.
Notice of Reasons for Rejection for corresponding Japanese Application No. 2016-526637 dated Oct. 3, 2017 and English translation.

\* cited by examiner

*Primary Examiner* — Scott Long
*Assistant Examiner* — Paul Martin
(74) *Attorney, Agent, or Firm* — Pearne & Gordon LLP

(57) ABSTRACT

The present invention relates to a method for producing a composition containing isomaltulose from a substrate containing sucrose comprising the steps of: a) contacting the substrate containing sucrose with a particulate carrier-immobilized sucrose isomerase biomass and b) obtaining a composition containing isomaltulose, characterized in that the median particle size d(0.5) of the carrier-immobilized sucrose isomerase biomass is from 370 to 550 μm. The carrier can be an alginate or a polyvinyl alcohol carrier.

13 Claims, 3 Drawing Sheets

OPTIMIZED METHOD FOR PRODUCING A COMPOSITION CONTAINING ISOMALTULOSE

FIELD OF THE INVENTION

The present invention relates to a method for producing a composition containing isomaltulose from a substrate containing sucrose.

BACKGROUND OF THE INVENTION

It is known that isomaltulose (palatinose, 6-O-α-D-glucopyranosyl-D-fructose) can be produced by means of a biotechnological process through enzymatic isomerization from sucrose. Isomaltulose is a physiologically valuable sugar, with increasing significance as a sucrose substitute in foodstuffs and related products. Isomaltulose is acariogenic and has a low glycemic index while having essentially the same energy content as sucrose. Isomaltulose has been approved for use in foodstuffs since 2005. Isomaltulose serves also as raw material for the production of the sugar alcohol isomalt, a racemic mixture of 1,6-GPS (6-O-α-D-glucopyranosyl-D-sorbitol) and 1,1-GPM (1-O-α-D-glucopyranosyl-D-mannitol) as well as modifications thereof, in particular 1,6-GPS- or 1,1-GPM-enriched mixtures.

In the known biotechnological systems, sucrose is not completely isomerized enzymatically to isomaltulose. Rather, further isomerization products and byproducts are generated. Trehalulose is an important further isomerization product.

Trehalulose (1-O-α-D-glucopyranosyl-D-fructose) as a further important isomer of sucrose can be found in nature, for example in honey and, like isomaltulose, is not cariogenic.

Both isomers, isomaltulose and trehalulose, are known for example from EP 1 424 074 A1 as hetero-disaccharides which, compared to sucrose in the small intestine of human and animal consumers, have a reduced hydrolysis rate and present themselves as advantageous food components, in particular such that can keep blood sugar levels under better control.

Isomaltulose and trehalulose are produced on a large scale by using enzymatic rearrangement of immobilized bacterial cells or fragments thereof. In this respect, the α1-α2-glycosidic bond existing between the monosaccharide units of the sucrose disaccharide is isomerized into an α1-α6-bond with isomaltulose or an α1-α1-bond with trehalulose, respectively. This rearrangement of sucrose into the two acariogenic disaccharides takes place by catalysis of the bacterial enzyme sucrose isomerase (E.C. 5.4.99.11, synonym: sucrose mutase, saccharose mutase, sucrose isomerase, isomaltulose synthase). Microorganisms that have sucrose isomerase activity and which can be used in biotechnological processes, are in particular *Protaminobacter rubrum*, *Erwinia rhapontici*, *Pseudomonas mesoacidophila*, *Pantoea dispersa* and *Serratia plymuthica*. Depending on the organism used and the reaction conditions, the result of this reaction is a product mix, which can contain not only the desired acariogenic disaccharides isomaltulose and trehalulose in different proportions but also possibly unwanted monosaccharides, for example glucose and/or fructose, as well as oligomers.

EP 0 483 755 B1 discloses methods for the production of compositions containing trehalulose and isomaltulose, for which purpose *Pseudomonas mesoacidophila* MX-45 (FERM-BP 3619) or *Agrobacterium radiobacter* MX-232 (FERM-BP 3620) is used to obtain a product containing predominantly trehalulose.

The use of enzymatic activities from *Pseudomonas putida*, *Thermus ruber*, *Thermus aquatica* or *Pimelobacter* for producing compositions containing predominantly trehalulose from solutions containing sucrose is known from EP 0 794 259 B1.

EP 0 091 063 A2 and EP 0 625 578 A1 disclose methods for the production of isomaltulose using immobilized bacterial cells, in particular *Protaminobacter rubrum* (CBS 574.77). The disclosed methods are based on a solution containing sucrose, which is transformed into a product containing predominantly isomaltulose but also trehalulose, using immobilized cells.

The disclosed methods are all characterized by a limited activity of sucrose isomerase, and where in particular for large-scale production of isomaltulose, trehalulose or both, an improved process efficiency is desirable, in particular a faster turnover rate and/or increased conversion rate and/or yield.

Therefore, the present invention aims to solve the technical problem to overcome the aforementioned disadvantages and in particular to provide a method, in the frame of which a conversion of sucrose to a product containing isomaltulose and/or trehalulose is achieved that is improved as compared to the prior art. In particular, it is an aim of the present invention to provide an increased turnover rate and/or an increased rate of conversion and/or yield.

BRIEF SUMMARY OF THE INVENTION

The present invention solves the technical problem it aims to solve by providing the teaching according to the independent claim.

Specifically, the present invention provides the following teachings.

The present invention relates in particular to an inventive method for the production of a composition containing isomaltulose from a substrate containing sucrose comprising the following steps:

a) contacting the substrate containing sucrose with a particulate carrier-immobilized sucrose isomerase biomass and b) obtaining a composition containing isomaltulose, characterized in that the particulate carrier-immobilized sucrose isomerase biomass has a particle diameter dp of 100 to 1300 µm, in particular 100 to 900 µm.

The present invention relates in particular to an inventive method wherein the particulate carrier-immobilized sucrose isomerase biomass is spherical.

In a particularly preferred embodiment, the particulate carrier-immobilized sucrose isomerase biomass can have the shape of a cube, a plate, a particle, a fiber, particularly a hollow fiber, a sphere, a hollow sphere or a LentiKat®.

The present invention relates in particular to an inventive method wherein the weight ratio of sucrose isomerase biomass to carrier is 10 to 6, preferably 7, parts sucrose isomerase biomass to 6 to 2, preferably 3, parts carrier (each as dry mass).

In a particularly preferred embodiment, the weight ratio of sucrose isomerase biomass to carrier is 0.2 to 0.8, in particular 0.3 to 0.7, or preferably 0.4 to 0.6.

The present invention relates in particular to an inventive method wherein the composition containing isomaltulose contains trehalulose.

The present invention relates in particular to an inventive method wherein the sucrose isomerase biomass is carrier-immobilized by adsorption, bonding, in particular covalent bonding, crosslinking, encapsulation or entrapment immobilization.

The present invention relates in particular to an inventive method wherein the carrier is an alginate or polyvinyl alcohol carrier, in particular a sodium alginate carrier.

The present invention relates in particular to an inventive method wherein the sucrose isomerase biomass is a sucrose isomerase, a microorganism cell with sucrose isomerase activity or a cell-extract with sucrose isomerase activity.

The present invention relates in particular to an inventive method wherein the sucrose isomerase biomass originates from microorganisms of the genera *Escherichia, Salmonella, Serratia, Erwinia, Enterobacter, Klebsiella, Raoultella, Pectobacterium, Pseudomonas, Azotobacter, Pantoea, Leucanea, Protaminobacter* or *Bacillus* sp.

The present invention relates in particular to an inventive method wherein the sucrose isomerase biomass originates from *Protaminobacter rubrum, Klebsiella* sp., particularly strain LX3 or strain NK33-98-8, *Klebsiella pneumoniae*, especially strain 342; *Enterobacter* sp., particularly strain SZ62 or strain FMB1, *Erwinia tasmaniensis*, particularly strain Et1/99; *Pectobacterium atrosepticum*, particularly strain SCRI 1043; *Pectobacterium carovotum*, particularly subspecies *brasiliensis*, particularly strain PBR 1692, *Azotobacter vinelandii, Leucanea leucocephalia, Erwinia rhapontici, Raoultella planticola, Pseudomonas mesoacidophila, Leuconostoc mesenteroides, Pantoea dispersa, Serratia plymuthica, Serratia marcescens* or *Agrobacterium radiobacter*.

The present invention relates in particular to an inventive method wherein the process steps a) and b) are carried out in a fixed bed or stirred tank.

The present invention particularly relates to an inventive method, wherein the obtained composition containing isomaltulose is hydrogenated catalytically.

The inventive method is preferably carried out continuously, but it can also be carried out semi-continuously or batch-wise.

The present invention relates in particular to an inventive method for producing a composition containing sugar alcohol, wherein an inventive method for producing a composition containing isomaltulose made from a substrate containing sucrose and then a catalytic hydrogenation of the resultant composition containing isomaltulose are carried out and a composition containing sugar alcohol is obtained.

The present invention also relates to a method for producing a composition containing sugar alcohol according to the present invention, wherein the composition containing sugar alcohol is isomalt or an isomalt variant.

In connection with the present invention, a "substrate containing sucrose" means a composition containing 1 to 100% by weight, preferably 1 to 99% by weight, preferably 10 to 95% by weight, in particular 20 to 90% by weight of sucrose (in each case referring to the weight of the dry substance of the substrate).

In one embodiment, the substrate containing sucrose can consist solely of sucrose.

In another embodiment, the substrate containing sucrose can, in addition to sucrose, contain one, two, three, several or many more substances, in particular selected from the group consisting of trehalulose, isomelezitose, glucose, fructose, sucrose, isomaltose, trisaccharides and oligomers.

In a particularly preferred embodiment, the substrate containing sucrose preferably has a sucrose content preferably of 2% by weight to preferably 85% by weight, preferably of 3% by weight up to preferably 90% by weight, preferably from 4% by weight up to preferably 95% by weight, preferably of 5% by weight up to preferably 96% by weight, preferably from 6% up to preferably 97% by weight, preferably from 7% by weight up to preferably 98% by weight, preferably from 8% up to preferably 99% by weight, preferably from 9% up to preferably 100% by weight, preferably from 10% by weight up to preferably 85% by weight, preferably from 20% by weight up to preferably 90% by weight, preferably from 30% by weight up to preferably 95% by weight, preferably from 40% by weight up to preferably 96% by weight, preferably from 50% by weight up to preferably 97% by weight, preferably from 60% by weight up to preferably 98% by weight, preferably from 70% by weight up to preferably 99% by weight or preferably from 80% by weight up to preferably 100% by weight (in each case referring to the weight of the dry substance of the substrate).

In a particularly preferred embodiment, the substrate containing sucrose includes a content of sucrose of preferably 5% by weight up to preferably 75% by weight, preferably of 10% by weight up to preferably 78% by weight, preferably of 20% up to preferably 85% by weight, preferably of 30% by weight up to preferably 88% by weight, preferably of 40% by weight up to preferably 93% by weight, preferably of 50% by weight up to preferably 94% by weight, preferably of 60% by weight up to preferably 95% by weight, preferably of 65% by weight up to preferably 96% by weight, preferably of 10% by weight up to preferably 97% by weight, preferably of 20% by weight up to preferably 98% by weight, preferably of 30% by weight up to preferably 99% by weight, preferably of 40% up to preferably 100% by weight (in each case referring to the dry matter weight of the substrate).

Especially preferred is a sucrose content of preferably 60 to 90% by weight, preferably 70 to 80% by weight, preferably 30 to 60% by weight, preferably 40 to 50% by weight (in each case referring to the weight of the dry substance of the substrate containing sucrose).

In a particularly preferred embodiment, the substrate containing sucrose comprises 90 to 99% by weight, preferably 90 to 98% by weight, in particular 90 to 97% by weight of sucrose (based in each case on the dry matter weight of the substrate).

In a particularly preferred embodiment, the substrate containing sucrose is present in liquid form, preferably in dissolved or suspended form, preferably in a liquid, particularly aqueous, medium. In a particularly preferred embodiment, the aqueous medium is water. In a particularly preferred embodiment, the substrate containing sucrose is present in an aqueous medium, namely in an aqueous solution or aqueous suspension.

In a particularly preferred embodiment, the aqueous medium containing the substrate that contains sucrose, i.e. for example the solution or suspension, comprises 0.1 to 80% by weight, preferably 1 to 70% by weight, preferably 4 to 60% by weight, preferably 5 to 50% by weight, especially 5 to 40% by weight, especially from 5 to 30% by weight, preferably from 35 to 45% by weight, preferably from 20 to 27%, preferably 40 to 75% by weight, especially 40 to 60% by weight, especially 10 to 60% by weight, preferably 20 to 55% by weight of the substrate containing sucrose, wherein these quantity ranges add up with the weight of the medium, i.e. for example water, to 100% (% by weight, each referring to the total weight of the medium containing the sucrose containing substrate, corresponding to the dry matter content of the substrate that contains sucrose in the medium).

In a particularly preferred embodiment, the solution or suspension that contains the sucrose-containing substrate can be thin juice or thick juice from a sugar processing plant, preferably with a dry matter content of 5 to 70%, preferably from 50 to 70%, in particular 55 to 68%, particularly from 5 to 30%, preferably 20 to 27% (% by weight, in each case referring to the total weight of the medium containing the sucrose substrate).

According to the invention it is also possible to use molasses or other impure compositions containing sucrose as a sucrose-containing substrate medium, in particular a solution or suspension.

In a further preferred embodiment, the liquid medium containing the sucrose-containing substrate, in particular the solution or suspension that contains the sucrose-containing substrate, has a sucrose content of 0.1 to 80% by weight, 5 to 30% by weight, 20 to 30% by weight, 20 to 60% by weight, 30 to 60% by weight, 35 to 45% by weight, 40 to 75% by weight, 40 to 60% by weight, 10 to 60% by weight or preferably 20 to 55% by weight (in each case referring to the total weight of the liquid medium containing the sucrose).

In connection with the present invention, a "composition containing isomaltulose" is understood to be the product of isomerization of the activity of a sucrose isomerase on a substrate containing sucrose. A composition containing isomaltulose of the present invention contains a mixture of isomaltulose and trehalulose, in particular consists thereof. Preferably, in one embodiment, more isomaltulose than trehalulose is present, and in another embodiment more trehalulose is present than isomaltulose. Further components of a composition containing isomaltulose can be isomelezitose, fructose, glucose, isomaltose, saccharose, trisaccharides, oligomers, or mixtures of two or more of these sugars.

Particularly preferably, the proportion of isomaltulose in the composition containing isomaltulose is at least 80% by weight, preferably at least 81% by weight, at least 82% by weight, at least 83% by weight, at least 84% by weight, at least 85% by weight, preferably at least 86% by weight and in particular at least 87% by weight, at least 88% by weight, at least 89% by weight, at least 90% by weight, at least 91% by weight, at least 92% by weight or 93% by weight (in each case referring to the dry matter of the composition containing isomaltulose). The rest of the components adding up to a 100% of such a composition containing isomaltulose are formed by trehalulose and optionally isomelezitose, fructose, glucose, sucrose, isomaltose, trisaccharides, oligomers or two or more thereof.

In a particularly preferred embodiment, the composition containing isomaltulose comprises 60 to 98% by weight, in particular 70 to 95% by weight, preferably 75 to 88% by weight, in particular 75 to 84% by weight isomaltulose (in each case referring to the dry matter of the composition containing isomaltulose).

In a further preferred embodiment, the composition containing isomaltulose can comprise from 1 to 20% by weight, 5 to 20% by weight, 10 to 30% by weight or 20 up to 99% by weight, preferably 20 to 40% by weight, preferably 20 to 30% by weight, preferably from 30 up to preferably 95% by weight, preferably from 45 to 96% by weight, preferably from 46 to 97% by weight, preferably from 47 to 98% by weight, preferably from 48 to 99% by weight, preferably from 49 to 99% by weight, preferably from 40 up to 98% by weight, preferably from 50 to 97% by weight, from 60 to 96% by weight or preferably from 70 up to 97% by weight, preferably from 80 up to 98% by weight, preferably from 75 up to 98% by weight, particularly 50 to 99% by weight, particularly 60 to 98% by weight, particularly from 85 up to 99% by weight and preferably 95% by weight to 99% by weight, preferably from 96 to 99% by weight, preferably from 97 to 99% by weight, preferably from 98 to 99% by weight of trehalulose (in each case referring to the dry matter of the composition containing isomaltulose). The rest of the components adding up to a 100% of the total composition is formed by isomaltulose and optionally glucose, fructose, isomelezitose, isomaltose, sucrose, trisaccharides, oligomers or two or more of them.

In a particularly preferred embodiment, the composition containing isomaltulose is 60 to 90% by weight of isomaltulose, 5 to 40% by weight of trehalulose and 0 to 5% by weight of at least one further substance selected from the group consisting of isomelezitose, sucrose, fructose, glucose, isomaltose, trisaccharides and oligomers.

In a further preferred embodiment, the present composition containing isomaltulose is 60 to 90% by weight of trehalulose, 5 to 40% by weight of isomaltulose and 0 to 5% by weight of at least one further substance selected from the group consisting of isomelezitose, fructose, glucose, sucrose, isomaltose, trisaccharides and oligomers.

In a further preferred embodiment, the present composition containing isomaltulose is in liquid form, preferably in dissolved or suspended form, preferably in a liquid, particularly aqueous, medium. In a particularly preferred embodiment, the aqueous medium is water. In a particularly preferred embodiment, the composition containing isomaltulose is in an aqueous medium, namely in an aqueous solution or aqueous suspension.

In a particularly preferred embodiment, the aqueous medium containing the composition that contains the isomaltulose, i.e. for example the solution or suspension, comprises 0.1 to 80% by weight, preferably 1 to 70% by weight, preferably 4 to 60% by weight, preferably 5 to 50% by weight, especially 5 to 40% by weight, especially from 5 to 30% by weight, preferably from 35 to 45% by weight, preferably from 20 to 27%, preferably 40 to 75% by weight, especially 40 to 60% by weight, especially 10 to 60% by weight, preferably 20 to 55% by weight of the substrate containing isomaltulose, wherein these quantity ranges add up with the weight of the medium, i.e. for example water, to 100% (% by weight, each referring to the total weight of the medium containing the composition that contains isomaltulose, corresponding to the dry matter content of the composition containing isomaltulose in the medium).

In connection with the present invention, the "sucrose isomerase biomass" is a biomass, in particular a cell, a cell extract, an enzyme or an enzyme mixture, wherein the biomass is capable under appropriate conditions of converting a substrate containing sucrose into a composition containing isomaltulose, i.e. exhibiting a sucrose isomerase activity. Preferably, the sucrose isomerase has the activity of a glucosyl transferase or of a sucrose-6-glucosyl mutase (EC 5.4.99.11).

In an advantageous way, the cells that can be used as sucrose isomerase biomass can be alive or dead. In a particularly preferred embodiment, the cells used as a sucrose isomerase biomass can be complete or destroyed, in particular ground cells, cell fragments, cell lysates or cell extracts. The inventively used sucrose isomerase biomass can in a preferred embodiment be purified, in particular be isolated, for example by conventional purification methods such as solvent extraction, French Press, lyophilization and/or enzymatic treatment. The sucrose isomerase biomass used can be of natural origin or it can be genetically modified in one embodiment.

The inventively provided step a) of contacting the substrate containing sucrose with a carrier-immobilized sucrose isomerase biomass is performed preferably according to the invention in such a way that a conversion of the substrate containing sucrose into a composition containing isomaltulose can take place, preferably in a way to optimize turnover.

Preferably, contacting is carried out at a temperature of 10 to 40° C., preferably 15 to 40° C., preferably 10 to 37° C., preferably 25 to 40° C., preferably 25 to 30° C., preferably 30 to 40° C., preferably 10 to 25° C., preferably 15 to 30° C., preferably 18 to 26° C., preferably 10 to 20° C., in particular 10 to 17° C.

In a further preferred embodiment, it is provided that the method step a) is carried out at a pH value from 5.0 to 9.0, preferably 5.0 to 7.0, preferably 6.0 to 7.0.

In connection with the present invention, carrier-immobilized sucrose isomerase biomass is understood to be a sucrose isomerase biomass immobilized at or in a carrier. This will be referred to below as immobilisate. Immobilization can have occurred in a conventional manner, for example by adsorption, bonding, in particular covalent bonding, crosslinking, encapsulation or entrapment immobilization.

In a particularly preferred manner, the present invention aims to produce the particulate carrier-immobilized sucrose isomerase biomass by supplying biomass in a first method step x1), for example by extraction in a fermenter, and by mixing this biomass in a second method step x2) with an alginate solution and introducing, especially by dripping, the biomass-alginate mixture in a third method step x3) into a calcium salt solution, especially a calcium chloride or calcium acetate solution. The particles that are forming will gel and in a fourth method step x4) are dried, for example in a fluidized bed dryer.

In a particularly preferred embodiment, it can also be provided to concentrate, i.e. thicken, the supplied biomass provided in the first method step x1) before mixing it with the alginate solution.

In a particularly preferred embodiment, in step x3) it is provided to introduce the biomass-alginate mixture into a calcium chloride solution by dripping under pressure, in particular by means of compressed air, i.e. in a blow-off method. In a further preferred embodiment, in step x3), the biomass-alginate mixture can be dripped into the calcium salt solution by means of an electrostatic process, in particular under the application of a voltage to the calcium-salt solution and the biomass-alginate mixture. In a further embodiment, the process step x3) can be carried out by vibrating the biomass-alginate mixture, for example by means of a punch, thus allowing a targeted dropping of this mixture into the calcium salt solution. Where appropriate, an increased pressure, for example, an increased air pressure, can be used.

In a further embodiment, the biomass-alginate mixture can be dripped into the calcium salt solution in method step x3) using a lateral blow-off pressure. In a further preferred embodiment, in step x3), the biomass-alginate mixture can be placed on a rotating disk and in this way can drip into the calcium salt solution. In a further preferred embodiment, the biomass-alginate mixture can be dripped into the calcium salt solution in method step x3) by means of rotating nozzles.

In a further preferred embodiment, the biomass-alginate mixture can be dripped into the calcium salt solution in method step x3) by means of a Jet-Cutter®. In a further preferred embodiment, the biomass-alginate mixture in method step x3) can be dripped into the calcium salt solution by means of multi-nozzle systems in combination with belt dryers and air drying, optionally with the use of cutting tools.

The aforementioned method steps, in particular the immobilization techniques described above according to process step x3), provide in an advantageous way the inventively preferred particle diameter dp.

In connection with the present invention, a particulate carrier-immobilized sucrose isomerase biomass is understood to be a carrier-immobilized sucrose isomerase biomass which is present in particle form, i.e. that are present in the form of particles, in particular in the form of solid particles.

In a preferred embodiment, the particulate carrier-immobilized sucrose isomerase biomass has, in dry form, a particle diameter dp of 100-1300 μm, preferably 200-1300 μm, preferably 150-1200 μm, preferably 150 to 1000 μm, preferably 100 to 900 μm, preferably 150 to 950 μm, preferably 150 to 900 μm, preferably 150 to 850 μm, in particular 100 to 800 μm, preferably 200 to 800 μm, in particular 200 to 950 μm, in particular 250 to 500 μm, in particular 300 to 700 μm, preferably 400 to 600 μm, in particular 450 to 550 μm, in particular 480 to 540 μm, preferably 500 μm (in each case referring to the dry support-immobilized sucrose isomerase biomass).

The present invention relates in particular to an inventive method wherein the particulate carrier-immobilized sucrose isomerase biomass has a particle diameter dp of 400 to 600 μm, in particular 100 to 400 μm, in particular 100 to 300 μm, in particular 200 to 300 μm, preferably 250 to 300 μm.

In a particularly preferred embodiment, the particulate carrier-immobilized sucrose isomerase biomass has a particle diameter dp of 250 to 500 μm.

In a particularly preferred embodiment, the particulate support-immobilized sucrose isomerase biomass in dry form has a volumetric mean value D[4,3] in the range from 380 to 570 μm, in particular a volumetric mean value D[4,3] in the range from 380 to 400 μm, 450 to 490 μm or 530 to 580 μm.

In a further preferred embodiment, the particulate support-immobilized sucrose isomerase biomass in dry form has a D[3,2] value in a range from 360 to 540 μm, especially 360 to 380, 430 to 450 or 510 to 530 μm.

In a further preferred embodiment, the particulate support-immobilized sucrose isomerase biomass in dry form has a specific surface area in a range from 0.0100 to 0.0180, in particular in a range from 0.0100 to 0.0118 or 0.0130 to 0.0140 or 0.0150 to 0.0170 m$^2$/g.

In a further particularly preferred embodiment, the particulate support-immobilized sucrose isomerase biomass in dry form has a uniformity in a range from 0.190 to 0.210.

In a further preferred embodiment, the particulate support-immobilized sucrose isomerase biomass has a d(0.1) value in a range from 270 to 400 μm, in particular in a range from 270 to 290 μm, 320 to 340 μm or 380 to 400 μm.

In a further preferred embodiment, the particulate support-immobilized sucrose isomerase biomass in dry form has a d(0.5) value in a range from 370 to 550 μm, in particular 370 to 390 μm, 450 to 470 μm or 530 to 550 μm.

In a further preferred embodiment, the particulate support-immobilized sucrose isomerase biomass in dry form has a d (0.9) value in a range from 510 to 760 μm, particularly 510 to 530 μm, 610 to 640 μm or 730 to 760 μm.

Unless otherwise stated in the present teaching, all parameters specified for the characterization of the particulate support-immobilized sucrose isomerase biomass, such as the specific surface area, the particle diameter, the volumetric mean values or the d (0.1), d (0.5), d (0.9) values, refer to particles measured in dry form.

In a particularly preferred embodiment, the particulate support-immobilized sucrose isomerase biomass in dry form has a particle diameter dp of 100 to 500, especially 100 to 450, especially 100 to 400, especially 100 to 300, especially 200 to 300, preferably 250 to 300 μm.

In connection with the present invention, the term "d(0.5) value" or the term "particle diameter d(0.5)" denotes the median value of the particle size distribution based on the mass or volume distribution, wherein d(0.5) indicates that 50% of particulate matter is less than the respective value specified.

Correspondingly, the term d(0.1) respectively d(0.9) means that 10 resp. 90% of the particulate matter is less than the respective value specified.

The particle size distribution is a volumetric particle size distribution.

In a particularly preferred embodiment, the determination of the particle size distribution of the produced particulate support-immobilized sucrose isomerase biomass is carried out by using laser diffraction, in particular according to the procedure of example 1 of the present teaching.

In a particularly preferred embodiment, the particulate carrier-immobilized sucrose isomerase biomass is spherical.

The carrier-immobilized sucrose isomerase biomass in a preferred embodiment has a uniformity coefficient <1, 2.

The uniformity coefficient is calculated using the following formula.

$$\text{Uniformity coefficient} = \frac{X_i |d(x, 0.5) - d_i|}{d(x, 0.5) X_i}$$

In a particularly preferred embodiment, the carrier-immobilized sucrose isomerase biomass has a specific activity of at least 400 units/g dry matter, preferably at least 450 units/g dry matter, preferably at least 500 units/g dry matter, especially at least 600 units/g dry matter, especially at least 700 units/g dry matter, preferably at least 800 units/g dry matter.

In connection with the present invention, a method according to the present invention is understood to mean in particular a method according to the above steps a) and b) for obtaining a composition containing isomaltulose, wherein the particulate carrier-immobilized sucrose isomerase biomass has a particle diameter dp of the above characterized inventive kind, in particular from 100 to 1300 μm, in particular from 150 to 1300 μm, preferably from 100 to 900 μm (in each case measured in dry form). A method of the present invention is also an especially advantageous embodiment of such a method, wherein the various specific embodiments of the inventive method can also be combined with one another, inasmuch as these combinations do not technically exclude one another.

Further advantageous embodiments of the invention result from the dependent claims.

The invention is further illustrated by way of the following examples and the corresponding figures.

DESCRIPTION OF THE DRAWINGS

The figures show.

DETAILED DESCRIPTION OF THE INVENTION

Example 1

Figure 1:
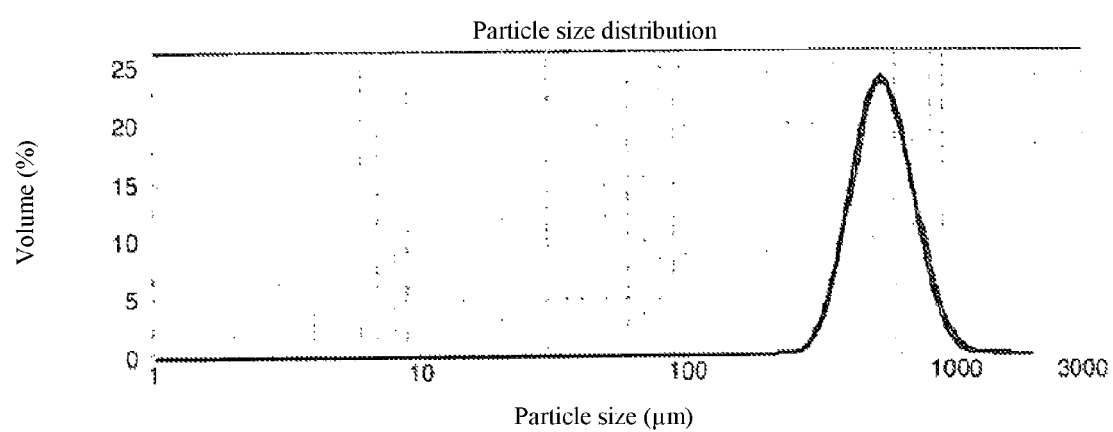
FIG. 1 graphically illustrates the size distribution of a first inventive particle preparation (coarse grain)
Figure 2:
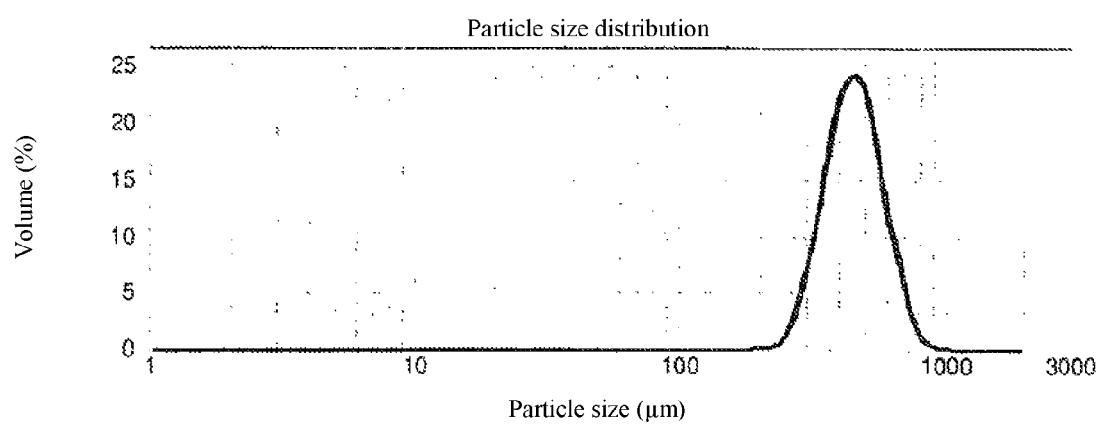
FIG. 2 shows the size distribution of a second inventive particle preparation (normal grain)
Figure 3:
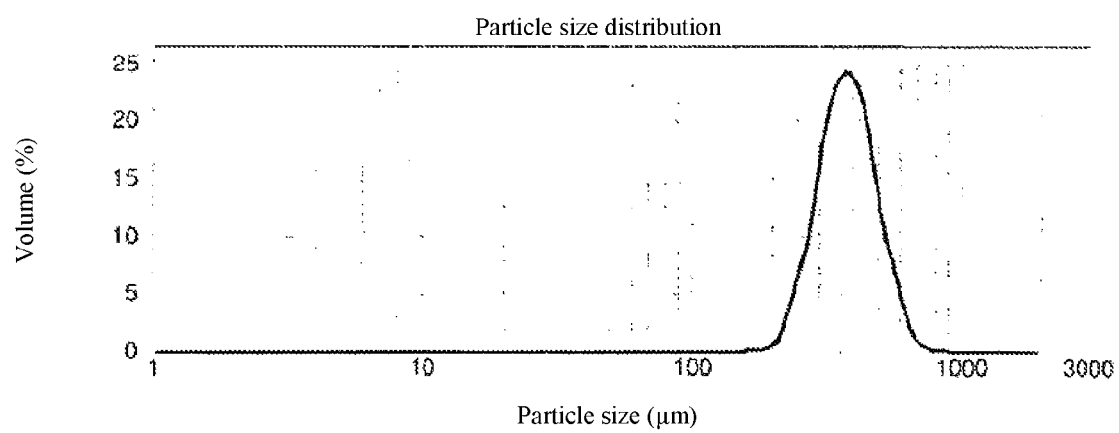
FIG. 3 shows the size distribution of a third inventive particle preparation (fine grain).

Determination of particle size distribution of immobilized biocatalysts by means of laser diffraction using a particle size analyzer (MASTERSIZER 2000, Malvern Instruments Ltd.) dry measurement.

Execution

With the help of laser diffraction measurement, the particle size distribution of the biocatalyst (immobilisate) according to the invention is determined. To describe the size distribution, the parameters $d_{0.1}$, $d_{0.5}$, $d_{0.9}$ and the uniformity are shown.

Short Description

The measurement principle is based on the scattered light/laser diffraction spectroscopy ISO 13320. Scattered particles are brought in low concentration into a laser beam. The introduction of the particles is effected by sucking the dry biocatalyst sample into the measuring cell ("dry measurement"). Depending on the diameter of the particles, there is a diffraction of the laser light that is collected by detectors as the scattered radiation. The result of the measurement is initially in the form of light intensities measured at the detectors and must be converted into a particle size distribution. This is achieved using the customary evaluation software for particles >1 μm given here by an approximation of Joseph von Fraunhofer (1814).

Equipment/Means

Test sieve with a diameter of 200 mm in accordance with DIN ISO 3310-1 of mesh size 1.25 mm
Collecting tray and cover for the test sieve
Malvern MASTERSIZER 2000 with dry dispersion unit Scirocco 2000 (A), including associated control and analysis software, Malvern Instruments Ltd.

Sample Preparation

All weighing operations are performed at ±0.01 g (reading accuracy).
Determine tare weights (tare) of the sieve and of the collecting tray
Assemble collecting tray and sieve
Determine weight of the complete biocatalyst sample (usually in a 250-mL vial) of each of the biocatalyst batch
Transfer sample quantitatively onto the sieve, cover it and sieve by hand
After sieving, weigh both the sieve with the residue and the collecting base with the passed volume (gross)
Evaluation/calculation: the percentage of coarse fraction of the biocatalyst sample is determined from the sieve residue
The sieve residue is discarded and the passed volume in the collecting tray is returned to the original sample bottle Measurement with the Malvern MASTERSIZER 2000

Dosing/Feeding of the Sample

The dosage of the samples is carried out via a vibrating channel with adjustable gap width. A coarse sieve with several balls is used as sieve strainer.

The dosage (gap width) needs to be adjusted depending on the product so that the measured concentration (green area) is achieved.

Dispersing Medium

Air with a certain pressure is used as a dispersing medium.

The measurements are performed with the MASTER-SIZER 2000, dispersing unit Scirocco 2000 (A).

Example 2

A. Preparation of the Biocatalyst

Cells from an inoculation of the strain *Protaminobacter rubrum* (CBS 574.77) are washed off with 10 ml sterile nutrient substrate consisting of 8 kg thick juice from a sugar plant (dry substance content=65%), 2 kg of corn steeping liquor, 0.1 kg $(NH_4)_2 HPO_4$ and 89.9 kg distilled water, adjusted to pH 7.2 if necessary. This suspension is used as inoculum for the shaking machine pre-culture in 1 liter flasks containing 200 ml of nutrient solution of the above composition.

After a 30-hour incubation at 29° C., 18 liters of nutrient solution of the above composition are inoculated with 10 flasks each (total content 2 liter) in a 30-liter small fermenter and fermented at 29° C. with 20 liters of air per minute and a stirrer speed of 350 rpm.

After reaching germinal counts of more than $5 \times 10^9$ germs/ml, the fermentation is stopped; the cells are harvested from the fermenter solution by centrifugation and suspended in a 2% sodium alginate solution.

By using a rotation immobilization, a jet cutting process or pulsating drip method, in particular using electrostatic methods, blow-off or vibration methods, in particular by using a lateral blow-off pressure, rotating disks or rotating nozzles, the suspension is dripped in a 2% calcium chloride solution and the inventively preferred particle diameters and particle size distributions, in particular with a particle diameter dp of 250-500 µm (based on dry particles) are provided. Multi-nozzle systems using a belt dryer are also used.

Table 1 shows the characterizing parameters achieved for three exemplary obtained biocatalyst preparations, namely for a first preparation, referred to as coarse grain, a second preparation, referred to as normal grain, and a third preparation, referred to as fine grain.

The resulting immobilization balls are washed with water. This biocatalyst can be stored at +4° C. for several weeks.

B. Production of the Composition Containing Isomaltulose

The immobilized cells obtained as described in A are filled into a temperature-controlled column reactor, heated up to 25 to 30° C. and continuously passed through by a sucrose solution with 35 to 45% dry matter content. The flow rate is set such that at least 97% of the sucrose used is rearranged.

TABLE 2

| Used biocatalyst | Feed stream [mL/h] | Turnover rate Weight dm sucrose/w. dm immobilisates/h | rel. activity % |
|---|---|---|---|
| Mean value coarse grain | 120 | 2.3 | 95 |
| Mean value normal grain | 126 | 2.4 | 100 |
| Mean value fine grain | 149 | 2.8 | 118 |
| Production (800 kg dm) | 4500 l/h | 2.25 | 94 |

Table 2 shows the catalytic activity of immobilisates of different particle diameters according to Table 1 in a 100 ml fixed bed.

A HPLC analysis of the composition containing isomaltulose emerging from the column reactor resulted in the following composition:

TABLE 3

| Fructose | Glucose | Sucrose | Isomaltulose | Trehalulose | Isomaltose | DP-3 | Isomelizitose | residual saccharides |
|---|---|---|---|---|---|---|---|---|
| 2.7 | 2.0 | 0.9 | 85.1 | 8.0 | 0.8 | 0.3 | 0.3 | <0.1 |
| 2.7 | 2.0 | 0.9 | 85.2 | 8.0 | 0.7 | 0.2 | 0.2 | <0.1 |
| 2.7 | 2.0 | 0.9 | 85.3 | 7.8 | 0.8 | 0.2 | 0.3 | <0.1 |

Product range according to Table 2 (coarse grain, normal grain, fine grain) (indications in g/100 g dry matter).

D. Hydrogenation of the Composition Containing Isomaltulose

The respective preparations, freed from the residual sucrose, of the composition containing isomaltulose were continuously hydrogenated on Raney nickel at 80° C. with hydrogen gas under pressure of about 10 MPa. After nickel separation and purification by ion exchange, the preparations of the composition containing isomaltulose hydrogenated under neutral conditions had about the following composition:

TABLE 1

| | d(0,1) (µm) | d(0,5) (µm) | d(0,9) (µm) | Vol. mean value D[4,3] (µm) | D[3,2] (µm) | Spec. surface (m$^2$/g) | Uniformity |
|---|---|---|---|---|---|---|---|
| Coarse grain | 392.690 | 539.575 | 749.682 | 559.012 | 524.745 | 0.0114 | 0.207 |
| Normal grain | 335.826 | 457.546 | 626.839 | 470.798 | 444.496 | 0.0135 | 0.198 |
| Fine grain | 280.522 | 381.883 | 523.390 | 393.435 | 371.278 | 0.0162 | 0.202 |

TABLE 4

| | |
|---|---|
| Mannitol | 1.5% of dry matter |
| Sorbitol | 4.0% of dm |
| 1,6-GPS | 44.4% of dm |
| 1,1-GPS | 3.8% of dm |
| 1,1-GPM | 45.3% of dm |
| hydrogenated and non-hydrogenated oligomers | 1.0% of dm |

Example 3

To prepare this biocatalyst, cells from an inoculation of the strain *Pseudomonas mesoacidophila* MX-45 (FERM 1 1808) were washed off with 10 ml sterile nutrient substrate consisting of 8 kg thick juice from a sugar plant (dry substance content=65%), 2 kg of corn steeping liquor, 0.1 kg $(NH_4)_2 HPO_4$ and 89.9 kg distilled water adjusted to pH 7.2. This suspension is used as inoculum for the shaking machine pre-culture in a 1-liter flask containing 200 ml of nutrient solution.

After a 30-hour incubation at 29° C., 18 liters of nutrient solution of the above composition were inoculated with 10 flasks each (total content 2 liter) in a 30-liter small fermenter and fermented at 29° C. with 20 liters of air per minute and a stirrer speed of 350 rpm.

After reaching germinal counts of more than $5 \times 10^9$ germs/ml, the fermentation was stopped; the cells were harvested from the fermenter solution by centrifugation and suspended in a 2% sodium alginate solution.

By using rotation immobilization, a jet cutting process or pulsating drip method, in particular using electrostatic methods, blow-off or vibration methods, in particular by using a lateral blow-off pressure, rotating disks or rotating nozzle, the suspension is dripped into a 2% calcium chloride solution and the inventively preferred particle diameters and particle size distributions, in particular with a particle diameter dp according to table 1 (based on dry particles) are provided. Multi-nozzle systems using a belt dryer are also used.

The resulting immobilization balls were washed with water. This biocatalyst can be stored at +4° C. for several weeks.

In order to produce a composition containing isomaltulose, the immobilized cells of *Pseudomonas mesoacidophila* MX-45 (FERM 11808) obtained in such a way were filled into a temperature-controlled column reactor, heated up to 25 to 30° C. and continuously passed through by a sucrose solution with 35 to 45% dry matter content. The flow rate is set such that at least 97% of the sucrose used was rearranged.

A HPLC analysis of the composition containing isomaltulose emerging from the column reactor resulted in the following composition:

TABLE 5

| | |
|---|---|
| Fructose | 0.2% of dm |
| Glucose | 0.2% of dm |
| Sucrose | 1.0% of dm |
| Isomaltulose | 12.5% of dm |
| Isomaltose | 0.2% of dm |
| Trehalulose | 85.7% of dm |
| Oligomers (DP > 3) | 0.2% of dm |

The composition containing isomaltulose produced in this way was freed from the residual sucrose and continuously hydrogenated on Raney nickel at about 80° C. with hydrogen gas under pressure of 8 to 12 MPa.

After nickel separation and purification by ion exchange, the composition containing isomaltulose hydrogenated under neutral conditions had the following composition:

TABLE 6

| | |
|---|---|
| Mannitol | 0.4% of dm |
| Sorbitol | 1.0% of dm |
| 1.1-GPM | 57.7% of dm |
| 1.1-GPS | 34.4% of dm |
| 1.6-GPS | 6.4% of dm |
| hydrogenated and non-hydrogenated oligomers | 0.2% of dm |

In order to remove the hydrogenated and non-hydrogenated oligomers as well as sorbitol from the product by chromatographic separation, the chromatographic separation, after the hydrogenation with a chromatographic separation column, was performed with a strongly acidic cation exchange resin loaded with sodium or potassium ions.

The invention claimed is:

1. A method for producing a composition containing isomaltulose from a substrate containing sucrose, comprising the steps of:
   a) contacting the substrate containing sucrose with a particulate carrier-immobilized sucrose isomerase biomass, wherein the carrier is an alginate or polyvinyl alcohol carrier and b) obtaining a composition containing isomaltulose,
   characterized in that the median particle size d(0.5) of the carrier-immobilized sucrose isomerase biomass is from 400-470 µm.

2. The method according to claim 1, wherein the particulate carrier-immobilized sucrose isomerase biomass has d(0.5) from 450 to 470 µm.

3. The method according to claim 1, wherein the particulate carrier-immobilized sucrose isomerase biomass is spherical.

4. The method according to claim 1, wherein the weight ratio of sucrose isomerase biomass to carrier is 10 to 6 parts sucrose isomerase biomass to 6 to 2 parts of the carrier (in each case dry weight).

5. The method according to claim 1, wherein the composition containing isomaltulose contains trehalulose.

6. The method according to claim 1, wherein the sucrose isomerase biomass is carrier-immobilized by bonding, crosslinking or entrapment immobilization.

7. The method according to claim 1, wherein the sucrose isomerase biomass is a sucrose isomerase, a microorganism cell with sucrose isomerase activity or a cell-extract with sucrose isomerase activity.

8. The method according to claim 1, wherein the sucrose isomerase biomass originates from microorganisms of the genera *Escherichia, Salmonella, Serratia, Erwinia, Enterobacter, Klebsiella, Raoultella, Pectobacterium, Pseudomonas, Azotobacter, Pantoea, Leucanea, Protaminobacter, Leuconostoc, Agrobacterium* or *Bacillus* sp.

9. The method according to claim 8, wherein the microorganism is selected from the group consisting of: *Protaminobacter rubrum, Klebsiella* strain LX3 or strain NK33-98-8, *Klebsiella pneumonia* strain 342; *Enterobacter* sp strain SZ62 or strain FMB1, *Erwinia tasmaniensis* strain Et1/99; *Pectobacterium atrosepticum* strain SCRI 1043; *Pectobacterium carovotum* subspecies *brasiliensis* strain PBR 1692, *Azotobacter vinelandii, Leucanea leucocephalia, Erwinia rhapontici, Raoultella planticola, Pseudomonas*

*mesoacidophila, Leuconostoc mesenteroides, Pantoea dispersa, Serratia plymuthica, Serratia marcescens* or *Agrobacterium radiobacter*.

10. Method according to claim 1, wherein the method steps a) and b) are carried out in a fixed bed or stirred tank.

11. The method according to claim 1, wherein the obtained composition containing isomaltulose is catalytically hydrogenated.

12. The method of claim 1 further comprising a catalytic hydrogenation of the resultant composition containing isomaltulose to obtain a composition containing sugar alcohol.

13. The method of claim 12, wherein the composition containing sugar alcohol is isomalt or an isomalt variant.

\* \* \* \* \*